(12) United States Patent
Yousef (10) Patent No.: US 9,498,297 B2
(45) Date of Patent: Nov. 22, 2016

(54) MANIPULATOR FOR SURGICAL TOOLS

(71) Applicant: United Arab Emirates University, Al-Ain (AE)

(72) Inventor: Basem Fayez Yousef, Al-Ain (AE)

(73) Assignee: United Arab Emirates University, Al-Ain (AE)

( * ) Notice: Subject to any disclaimer, the term of this patent is extended or adjusted under 35 U.S.C. 154(b) by 619 days.

(21) Appl. No.: 13/864,858

(22) Filed: Apr. 17, 2013

(65) Prior Publication Data

US 2013/0282022 A1     Oct. 24, 2013

Related U.S. Application Data

(60) Provisional application No. 61/625,960, filed on Apr. 18, 2012.

(51) Int. Cl.
*A61B 34/00* (2016.01)
*A61B 17/34* (2006.01)

(52) U.S. Cl.
CPC ............... *A61B 34/30* (2016.02); *A61B 34/71* (2016.02); *A61B 90/11* (2016.02); *A61B 2017/3409* (2013.01)

(58) Field of Classification Search
CPC ............... A61B 19/20; A61B 19/201; A61B 90/10–90/13; A61B 34/30; A61B 34/71
USPC ............. 600/417, 424, 429; 606/1, 129, 130
See application file for complete search history.

(56) References Cited

U.S. PATENT DOCUMENTS

| | | | | |
|---|---|---|---|---|
| 3,858,702 A | * | 1/1975 | Azuma ................... | B41J 19/70 400/103 |
| 4,060,162 A | * | 11/1977 | Frechette ................ | B41J 35/04 400/144.2 |
| 4,608,977 A | * | 9/1986 | Brown ................... | A61B 19/201 378/162 |
| 5,201,742 A | * | 4/1993 | Hasson ................ | A61B 19/201 606/1 |
| 5,397,323 A | | 3/1995 | Taylor et al. | |
| 5,984,930 A | * | 11/1999 | Maciunas ............ | A61B 19/201 600/417 |
| 7,559,935 B2 | * | 7/2009 | Solar .................... | A61B 19/201 606/130 |
| 7,636,596 B2 | * | 12/2009 | Solar ................... | A61B 19/201 600/429 |

(Continued)

OTHER PUBLICATIONS

Bassan, H., et al., "A Novel Manipulator for Prostate Brachytherapy: Design and Preliminary Results." Proc. of the 4th IFAC Symposium on Mechatronics Systems, 2006, pp. 30-35.

(Continued)

*Primary Examiner* — Todd E Manahan
*Assistant Examiner* — Charles Wei
(74) *Attorney, Agent, or Firm* — Fitch, Even, Tabin & Flannery LLP (57) ABSTRACT

Apparatus 10 includes arcuate links 12, 14, a block-like hub 16 adapted to hold a surgical tool 50, and a frame 26 for supporting the links 12, 14. Each link 12, 14 includes a curved portion extending from a first extremity at an end of the link 12, 14 to an extremity at an opposite end thereof. The hub 16 is slidably mounted to the links 12, 14. The hub 16 moves along arcuate paths defined by the links 12, 14, for guiding manipulation of the tool 50 about a pivot point 40. The frame 26 includes a lateral wall having a first pair of opposed guiding slots 28 and a second pair of opposed guiding slots 29. The slots 28 slidingly receive the extremities of the link 12 and have a degree of curvature equivalent to the degree of curvature of the link 14. The slots 29 slidingly receive the extremities of the link 14 and have a degree of curvature equivalent to the degree of curvature of the link 12.

9 Claims, 5 Drawing Sheets

(56) References Cited

U.S. PATENT DOCUMENTS

| | | | | |
|---|---|---|---|---|
| 7,658,879 | B2* | 2/2010 | Solar | A61B 19/201 |
| | | | | 264/278 |
| 7,824,417 | B2* | 11/2010 | Magnusson | A61B 17/3403 |
| | | | | 606/130 |
| 2003/0125716 | A1* | 7/2003 | Wang | A61B 19/22 |
| | | | | 606/1 |
| 2003/0229338 | A1* | 12/2003 | Irion | A61B 19/26 |
| | | | | 606/1 |
| 2006/0229641 | A1* | 10/2006 | Gupta | A61B 17/3403 |
| | | | | 606/130 |
| 2012/0095449 | A1* | 4/2012 | Stefanchik | A61B 17/0218 |
| | | | | 606/1 |

OTHER PUBLICATIONS

Chinzei, Kiyoyuki, et al., "Towards MRI Guided Surgical Manipulator." Diagnostics and Medical Technology, Medical Science Monitor, 2001, vol. 7, No. 1, pp. 153-163.

Fichtinger, Gabor, et al., "System for Robotically Assisted Prostate Biopsy and Therapy with Intraoperative CT Guidance." Academy Radiology, 2002, vol. 9, pp. 60-74.

Kronreif, Gernot, et al., "Robotic Guidance for Percutaneous Interventions." Journal of Advanced Robotics, 2003, vol. 17, No. 6, pp. 541-560.

Stoianovici, Dan, et al., "AcuBot: A Robot for Radiological Interventions." IEEE Transactions on Robotics and Automation, vol. 19, No. 5, Oct. 2003, pp. 927-930.

* cited by examiner

MANIPULATOR FOR SURGICAL TOOLS

CROSS REFERENCE TO RELATED APPLICATION

This application claims the benefit of U.S. Provisional Application No. 61/625,960, filed on Apr. 18, 2012, which is incorporated herein by reference in its entirety.

FIELD OF THE INVENTION

This invention relates to robotic manipulators, in particular, remote center-of-motion (RCM) robots that can be used in medical applications to manipulate the orientation of end effectors such as surgical tools, which are commonly used for image guided, and/or robot assisted interventions. The RCM robot provides means for manipulating the tool about a desired pivot point, typically the tool's point of entry to the patient's body, hence enables both precise localized treatment delivery and convenient use of different tools for minimally invasive surgery tools.

BACKGROUND OF THE INVENTION

In recent years, robot-assisted procedures for surgery and therapy have received considerable attention and are often preferred over conventional, manually performed procedures because of a robot's ability to perform consistent precise movements free of fatigue and tremor, and carry out surgical procedures with high dexterity and accuracy beyond those of a surgeon.

However, many surgical applications require the ability to accurately and conveniently manipulate and re-orient a special purpose surgical tool, e.g. manipulation of laparoscopic cameras and external beam radiation, biopsy sampling, precise tissue removal, precise radioactive seed implantation for prostate and lung brachytherapies, localized drug delivery using needles, catheter insertion and the like. These applications require accurately controlled motion, e.g. re-orientation of a tool, under computer control, while strictly limiting undesired motions. Moreover, many of these applications require relatively slow computer-controlled precise motions. While it is difficult for a human surgeon to perform such motions, it can be easily accomplished consistently by utilizing a special purpose robotic mechanism to perform it.

It is worth noting that such procedures need the ability to manipulate and re-orient the tool (needle, surgical tool, saw, etc.) about a pivot point, also called Remote Center-of-Motion (RCM), typically it is the point of entry of a surgical tool into the patient's internal organs. In a conventional robot (e.g. industrial robots), motions about an RCM are achieved by coordinated motions of multiple joints, many of which may be required to move rapidly through a large workspace in order to achieve relatively small tool reorientations. Thus, relatively fast joint motions may be needed to cause quite rapid end effector re-orientation. This increases the potential to injuries and may cause collisions, i.e. robot-patient or robot-equipment collisions. Also when small joint actuators are used or joint velocities are limited for safety considerations, many desired tool motions may become extremely slow.

Also, because of the limited and constrained workspace of surgical environments, surgical mechanisms need to be designed with special configuration that allows for miniaturization and to have compact sizes in order to interact easily with the patient and other existing equipment. Again this enhances the robot's maneuverability but presents another challenge to the design and implementation of the mechanism kinematics, given the working volume restrictions.

Some robotic systems for needle insertion or tool re-orientation have been reported in the literature. The most notable being a system for the augmentation of surgery with a remote center-of-motion manipulator reported in [R. Taylor, J. Fonda, D. Grossman, J. Karidis and D. LaRose, "Remote Ceter-of-Motion Robot for Surgery", U.S. Pat. No. 5,397,323, 1995.]. It adopts a double parallelogram structure. However, its working radius forms a main trade off. If a large working radius for the tool is desired, the resulting robot structure can become somewhat clumsy and obstructive in the operating room and can impede access to the patient. Also, if the working radius is small, then the mechanism may get in the way of the surgeon's hands, instruments or direct vision.

A related consideration is that high quality mechanism can be expensive and difficult to fabricate. Another mechanism presented in [H. Bassan, R. V. Patel and M. Moallem, "A novel manipulator for prostate brachytherapy: Design and preliminary results", Proc. of the 4th IFAC Symposium on Mechatronics Systems, 2006, pp. 30-35.] was designed to perform an RCM. Since the main structure was based on the mechanism introduced by R. Taylor et. al., it demonstrated the same drawbacks mentioned above. Also, the PAKY/RCM was developed at Johns Hopkins University and reported in several publications [G. Fichtinger, T. L. DeWeese, A. Patriciu, A. Tanacs, D. Mazilu, J. A. Anderson, K. Masamune, R. H. Taylor, and D. Stoianovici, "System for robotically assisted prostate biopsy and therapy with intra-operative CT guidance", Journal of Academic Radiology, volume 9, 2002], [D. Stoianovici, K. Cleary, A. Patriciu, D. Mazilu, A. Stanimir, N. Craciunoiu, V. Watson, and L. Kavoussi, "Acubot: A robot for radiological interventions", IEEE Trans. on Robotics and Automation, volume 19, 2003]. The robot consists of three independent stages for needle positioning, orientation and insertion.

Another mechanism for needle insertion/reorientation is described in [K. Chinzei and K. Miller, "Towards MRI guided surgical manipulator", Int. Medical Journal for Experimental and Clinical Research, volume 7, 2001]. The design utilizes planar drives similar to that of Kronreif [G. Kronreif, M. Fürst, J. Kettenbach, M. Figl, and R. Hanel. Robotic guidance for percutaneous interventions. In Journal of Advanced Robotics, volume 17, 2003] to create an RCM. Again, the sizes of these manipulators are quite large and they are unsuitable for use in surgical applications.

SUMMARY OF THE INVENTION

There is provided a surgical manipulator (also called robot) with a special configuration that supports a remote center-of-motion attribute, so it can be used to reorient different kinds of surgical tools that need accurate manipulation about a pivot point, typically the point of entry to the internal organs of a patient, and that are commonly used in minimally invasive surgeries. Also, the robot's special configuration will allow for miniaturization.

The surgical manipulator has a special configuration that supports a remote center-of-motion attribute, that enables to accurately and conveniently manipulate and re-orient in 1 or 2 degrees of freedom, and to firmly "lock" in place, special purpose surgical tools necessary for minimally invasive therapy. The manipulator comprises a joint-link structure comprising arcuate joints (links) that enables comfortable manoeuvrability (manipulation) of the end effector or the surgical tool about a pivot point, typically the port of entry of the tool to the patient's body, while preventing the enlargement of the key hole, in the constrained and limited workspace of surgical environments. Also the configuration of the joint-link structure provides an open structure that keeps the robots' main parts out of the surgeon's field of view and out of the work area, providing sufficient space in the vicinity of the operative field, or the entry port of the tool to the patient's internal organs. The surgical manipulator can be used in manual, autonomous or remote-control modes.

The surgical manipulator (also called robot) is also adapted to overcome the size-related difficulties and problems associated with the limited workspace inherent in therapy since its configuration avoids the structural complexity associated with the existing robots, hence it is easy to be miniaturized. It is also adapted to achieve small-scale movement control for high precision manipulation of a surgical tool. The surgical manipulator operates with 2 degrees of freedom that enables controlling the motion of the joints either independently or simultaneously, hence acting as a 2 DoF or 1 DoF robot, as needed.

The surgical manipulator is also adapted to have an appropriate architecture that can be operated either manually, or autonomously with a simple and intuitive manipulation protocol to obviate the need for long training hours, hence providing the surgeon the ability to fully and easily exploit the dexterity of the robot. This also permits manipulation of different kinds of surgical tools necessary for minimally invasive therapy making it usable for simple or advanced surgical procedures.

The manipulator is also adapted to have a relatively light-weight and be cost effective to manufacture.

According to a first aspect of the invention, there is provided a manipulator apparatus for assisting surgery comprising a first arcuate link having a first center and a first degree of curvature and extending from a first extremity to a second extremity within a first plane of curvature containing the first arcuate link and the first center of curvature; and a hub having a vertical axis and adapted to receive a surgical tool having a pivot point along the vertical axis, the hub being adapted to be mounted to and engage with the first actuate link to move between the first and second extremities in a first movement route within the first plane of curvature such that the first center of curvature coincides with the pivot point of the surgical tool at any point within the first movement route for enabling rotation of the surgical tool about the pivot point in a first degree of freedom within the first plane of curvature.

Preferably, the manipulator apparatus further comprises a second arcuate link having a second center and a second degree of curvature and extending from a first extremity to a second extremity within a second plane of curvature containing the second arcuate link and the second center of curvature; wherein the hub is further adapted to be mounted to and engage with the second arcuate link between the first and second extremities in a second movement route within the second plane of curvature perpendicularly to the first plane of curvature such that the second center of curvature coincides with the pivot point of the surgical tool at any point within the second movement route for enabling rotation of the surgical tool about the pivot point in a second degree of freedom within the second plane of curvature, the second degree of freedom being perpendicular to the first degree of freedom.

Preferably, the manipulator apparatus further comprises a frame having a lateral wall for supporting the extremities of the arcuate links; and guiding means for enabling simultaneous lateral movement of both the first and second arcuate links along the lateral wall of the frame; wherein the guiding means and the arcuate links are adapted for enabling movement of the hub along a third movement route within a spherical plane surface having a center of sphere coinciding with the pivot point at any point within the third movement route for enabling rotation of the surgical tool about the pivot point in two degrees of freedom defined by the first and second degrees of freedom.

Preferably, the guiding means comprise guiding slots comprising: a first pair of guiding slots having a first degree of curvature equivalent to the degree of curvature of the second arcuate link, the first pair of guiding slots being adapted to guide the first arcuate link; and a second pair of guiding slots having a second degree of curvature equivalent to the degree of curvature of the first arcuate link, the second pair of guiding slots being adapted to guide the second arcuate link.

Preferably, the guiding means further comprise vertical rollers and shoulders adapted to engage together for preventing vertical motion of the arcuate links during movement of the hub for preventing or minimising deviation of the center of the sphere from the pivot point of the medical tool during the lateral movement of the arcuate links. Preferably, the guiding means also further comprise lateral rollers adapted to engage with the lateral wall of the frame for preventing radial motion of the arcuate links during movement of the hub for preventing or minimising deviation of the center of the sphere from the pivot point of the medical tool during the lateral movement of the arcuate links.

Preferably, each one of the arcuate links comprise a pair of curved rods defining an opening therebetween adapted to allow passage of the medical tool. Though, the arcuate links can also comprise a single arcuate rod instead of a pair of rods. Preferably, the hub has a lateral wall having openings adapted to receive the arcuate links in a concentric configuration with respect to the hub vertical axis for allowing the hub to slide along the curved rods in the first and second movement routes.

Preferably, the hub has substantially a rectangular shape having top and bottom walls and a first and second pairs of opposite side walls forming the lateral wall, wherein the top and bottom walls have openings aligned along the vertical axis for receiving the medical tool, and each opposite side walls of the hub has aligned openings adapted to receive each one of the arcuate links respectively.

Preferably, the apparatus further comprises a tool adapter adapted to be adjusted to different types and dimensions of medical tools, the hub being adapted to receive the medical tool through the medical adapter.

Preferably, the manipulator apparatus further comprises: a motor having a gear and a shaft, a rotary encoder and a cable for each one of the arcuate links; wherein the hub, the motor and the encoder are connected therebetween using the cable such that the motor actuates movement of the hub using the cable and the encoder measures the angular rotation of the cable for enabling determination of the position of the hub within the arcuate links.

Preferably, the motors are located at the first extremities of the arcuate links and the rotary encoders are located at the second extremities of the arcuate links.

Further advantages of the invention will become apparent from the drawings and the following description.

BRIEF DESCRIPTION OF THE DRAWINGS

The invention will now be described by way of example only, with reference to the accompanying drawings, in which.

DETAILED DESCRIPTION OF THE INVENTION

As shown in FIGS. 1 to 4, there is provided a surgical manipulator apparatus 10 comprising a joint-link structure 12 and/or 14 and a hub 16 adapted to receive a surgical tool 50 and to be mounted to and engage with the joint-link structure 12/14 such that it can move along the routes defined by the joint-link structure 12 and/or 14 for the manipulation of the surgical tool 50. The joint-link structure 12/14 comprises at least one arcuate links 12 and/or 14. Each arcuate link 12 or 14 will give an additional degree of freedom for the operation of the surgical tool manipulator apparatus. Using a single arcuate link will allow use of the surgical tool manipulator 10 for the manipulation of the surgical tool 50 according to one degree of freedom. Using the second arcuate link 14 along with the first arcuate link 12 will allow use of the surgical tool manipulator 10 for the manipulation of the surgical tool 50 in a second degree of freedom. It is also possible to use more than 2 arcuate links 12/14 to allow manipulation of the surgical tool according to additional degrees of freedom, however this will not be necessary since the simultaneous movements of the first and second arcuate links 12 and 14 as suggested in the present invention will allow to provide a 2 DoF manipulator 10 for the manipulation of the surgical tool 50.

Figure 1:
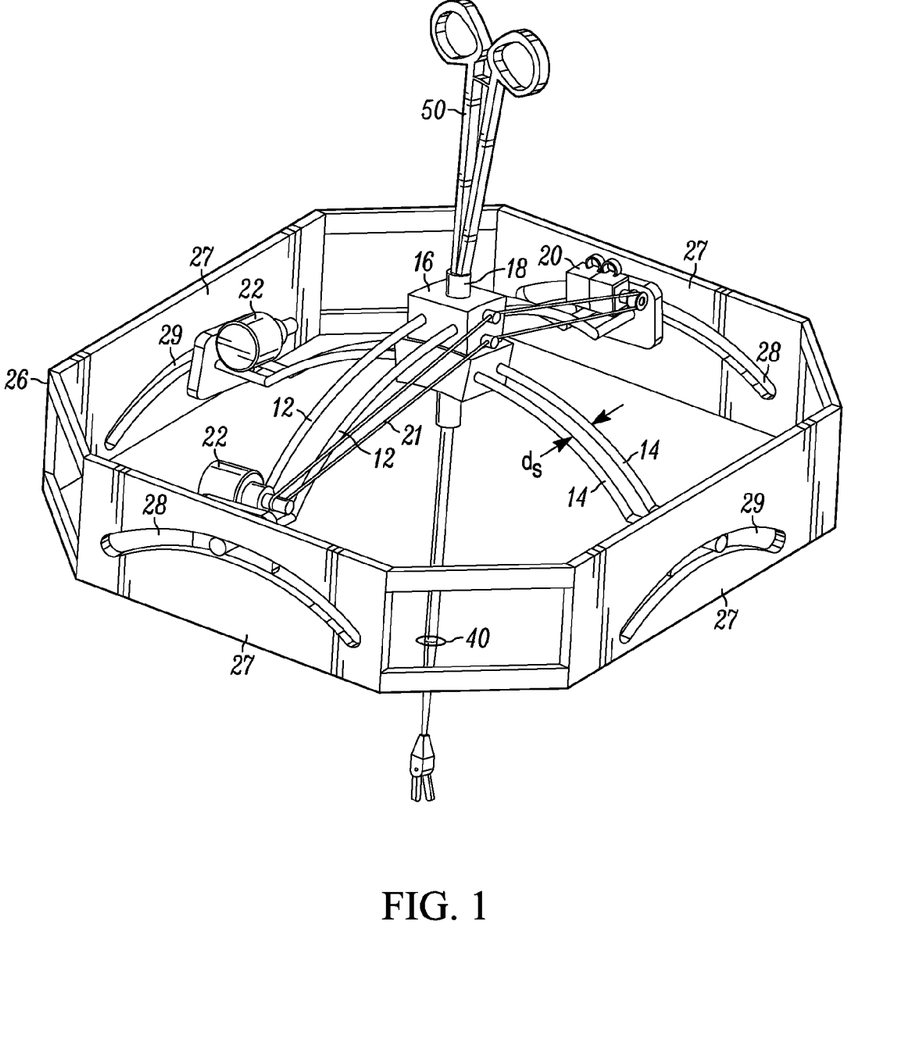
FIG. 1 is an isometric view showing a preferred embodiment of the surgical manipulator apparatus of the present invention employing a surgical tool that can be used for suturing and/or knot tying according to a preferred embodiment of the present invention (cable routing is only shown for one joint).
Figure 2:
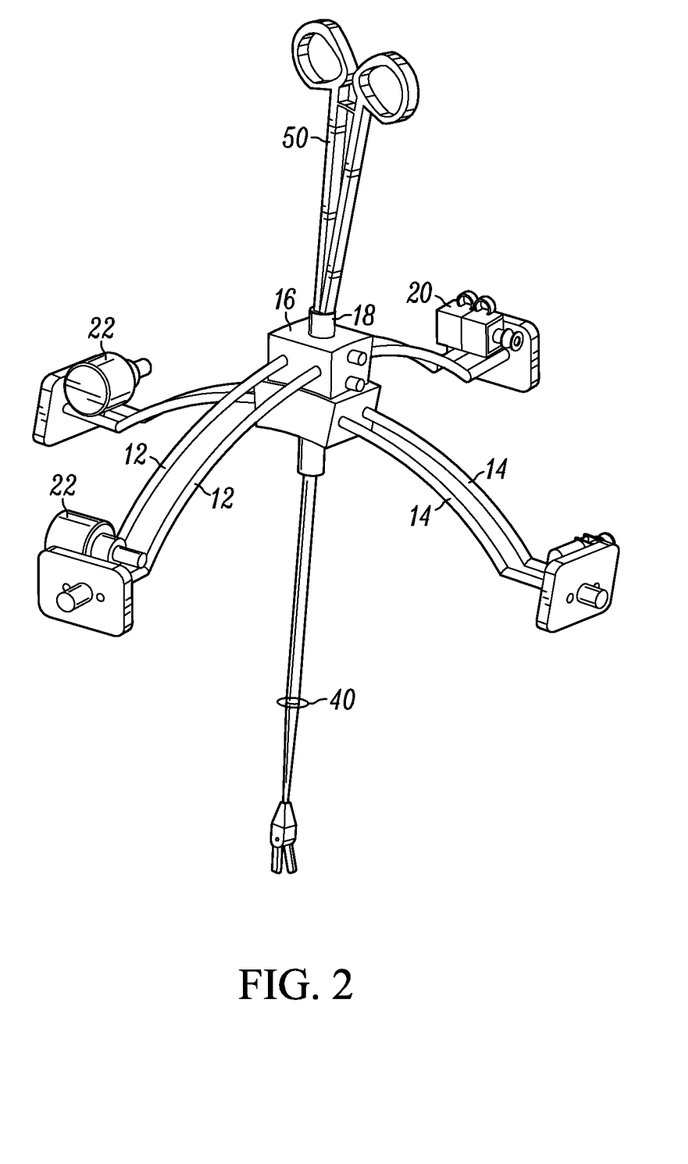
FIG. 2 is a perspective view of the arcuate links (joints) employing a surgical tool that can be used for suturing and/or knot tying showing the pivot point coinciding with the centers of the arcuate links (joints) according to a preferred embodiment of the present invention (no frame and cable routing shown).
Figure 3:
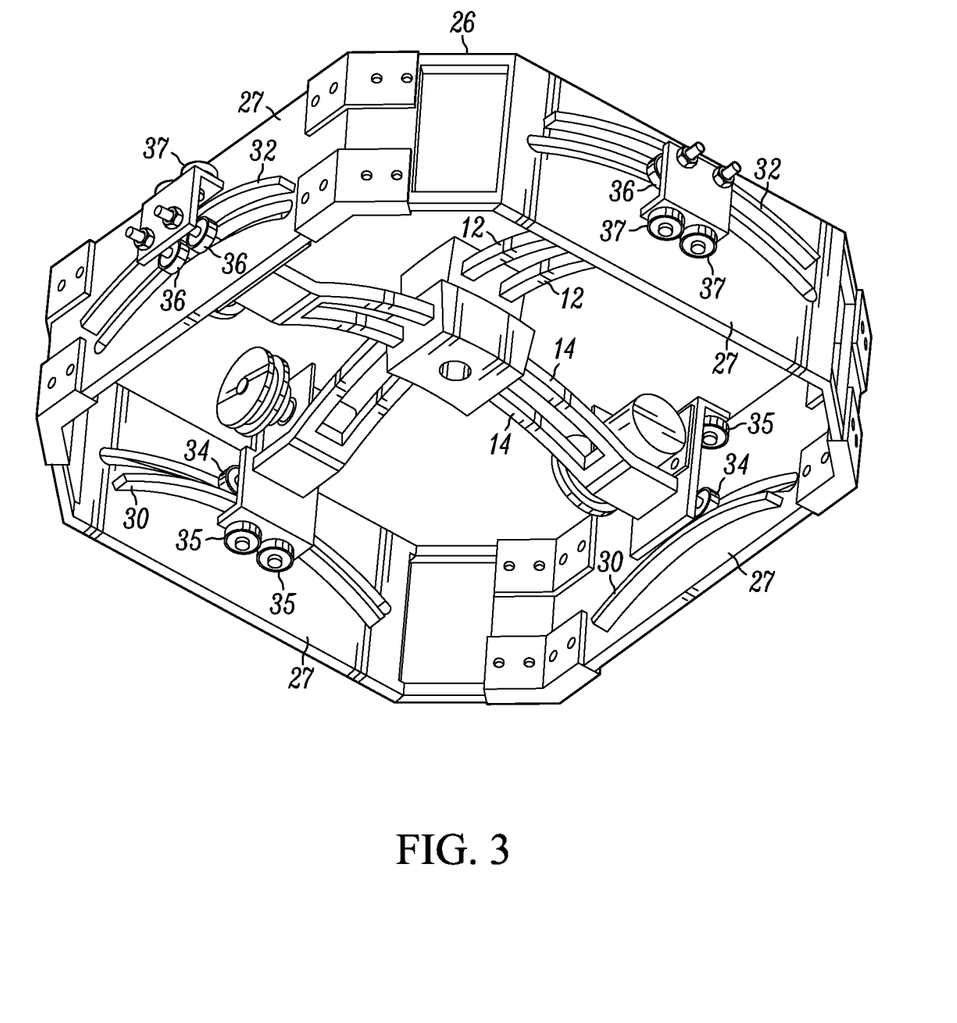
FIG. 3 is a perspective bottom view showing a manipulator apparatus of the present invention (no cable routing shown) according to a preferred embodiment of the present invention.
Figure 4:
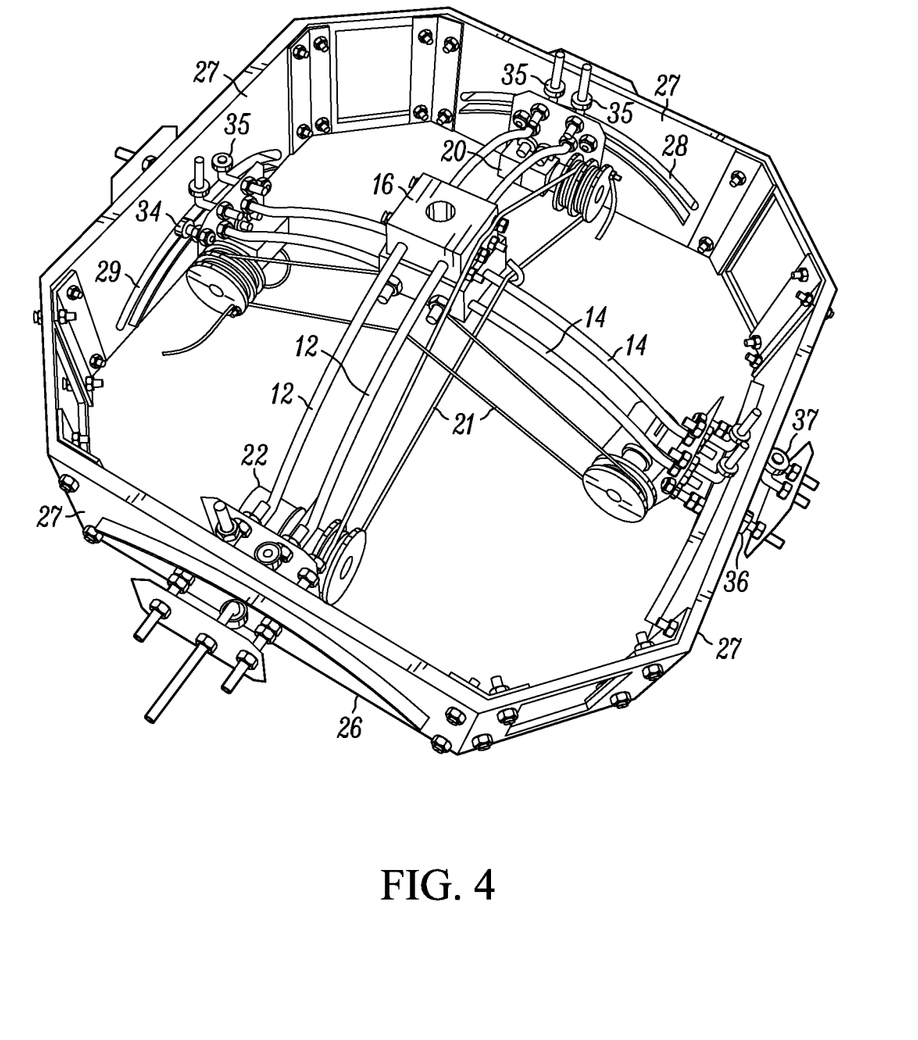
FIG. 4 is a perspective top view showing a manipulator apparatus according to a preferred embodiment of the present invention.

The hub 16 is preferably in the form of a rectangular block having top and bottom surfaces and lateral surfaces (a pair of opposite side surfaces). The hub 16 is at least partially hollow. The hub 16 has an opening at the top surface and an opening at the bottom surface aligned along a vertical axis. These openings are adapted to receive and securely hold a surgical tool adaptor 18 which is adapted to receive surgical tools of different dimensions. FIG. 2 shows a surgical tool 50 that can be used for suturing and/or knot tying inserted inside the tool adapter 18. The surgical tool 18 is inserted inside the tool adapter 16 and extends vertically along the vertical axis. The surgical tool 50 has an upper portion extending upwardly away from the top surface of the hub 16 and a lower portion extending downwardly below the bottom surface of the hub 16. The bottom portion of the surgical tool 50 has a pivot point 40 which corresponds to the entry point of the patient's body when the surgical manipulator 10 is used. When the surgical manipulator 10 is used in a manual mode, the upper portion of the surgical tool is used by the medical professionals to manipulate the surgical tool 50 to rotate the surgical tool around the pivot point. When the surgical manipulator operates in an autonomous mode, there is no need to have a portion of the medical tool extending upwardly above the top surface of the hub. The hub 16 can be of other forms, such as cylindrical for example.

The hub 16 is adapted to be mounted to and engage with the arcuate links 12 and 14 such that it can move along the tracks defined by the arcuate links 12 and 14 without deviating from the tracks (routes) defined by these arcuate links 12 and 14. When two arcuate links 12/14 are used by the manipulator 10, and even when the robot 10 is to be used as 1 DoF robot only, there is an advantage of being able to move the hub 16 along any one of the arcuate links 12/14 without being required to demount the hub 16 from one arcuate link to mount it on the other arcuate link. Accordingly, the hub 16 according to the preferred embodiment is adapted to engage both arcuate links 12/14 simultaneously such that moving the hub 16 along one arcuate link will result in dragging the other arcuate link along the same direction of the movement of the hub 16.

As one implementation for this solution, the hub is adapted to receive both arcuate links 12/14 through the hub's 16 lateral surface in such a manner that the arcuate links 12 and 14 are concentric to each other with respect to the vertical axis of the hub and located at two different levels along the vertical axis such that one of the arcuate links (the first arcuate link) is more distanced with respect to the pivot point 40 than the other one.

The first arcuate link 12 has a first center of curvature and extends from a first extremity to a second extremity within a first plane of curvature containing said first arcuate link 12 and the first center of curvature. The second arcuate link 14 has a second center of curvature extending from a first extremity to a second extremity within a second plane of curvature containing the second arcuate link and the second center of curvature.

Once mounted to only one arcuate link 12, the hub 16 is adapted to receive the surgical tool 50 having the pivot point 40 and to engage and slide along the first arcuate link 12 between the first and second extremities in a first movement route within the first plane of curvature such that the first center of curvature of the first arcuate link coincides with the pivot point 40 of the surgical tool 50 at any point within the first movement route for enabling rotation of the surgical tool 50 about the pivot point 40 in a first degree of freedom within the first plane of curvature.

Once mounted to both the first and the second arcuate links 12 and 14, the hub 16 is further adapted to receive and slide along the second arcuate link 14 between the first and second extremities in a second movement route within the second plane of curvature perpendicularly to the first plane of curvature such that the second center of curvature coincides with the pivot point 40 of the surgical tool 50 at any point within the second movement route for enabling rotation of the surgical tool 50 about the pivot point in a second degree of freedom within the second plane of curvature, where the second degree of freedom is perpendicular to the first degree of freedom.

This allows the hub 16 to move along two different degrees of freedom perpendicular to each other. Therefore, this allows for the manipulation of the surgical tool according to the first degree of freedom and to the second degree of freedom.

Each one of the arcuate links 12 and 14 preferably comprises a double-curved guidance links parallel to each other. The hub 16 preferably comprises curved guidance holes to allow the arcuate links 12/14 to pass through it. This allows the hub 16 to slide along the guidance links, and will prevent the hub 16 from spinning about the guidance links 12 and 14.

The structure of the double-curved rods 12 and 14 also allow for the tool adaptor 18 to pass between the double-curved rods 12 and 14. When the hub 16 slides along an arcuate link, the surgical tool 18 rotates about the pivot point 40 which is located at the center of the curvature of that arcuate link 12/14 (FIG. 2). This allows manipulating and reorienting the medical tool 50 in one DoF about the pivot point 40 where the rotation takes place in the plane that contains the arc of the link 12/14 on which the hub 16 movement takes place. A person skilled in the art would appreciate that the double-curved links 12 and 14 structure is not an absolute requirement in the sense that each one of the arcuate links can consist of a single rod/shaft, however certain measures have to be taken to prevent the hub 16 from spinning while in movement along the rod/shaft.

Figure 5:
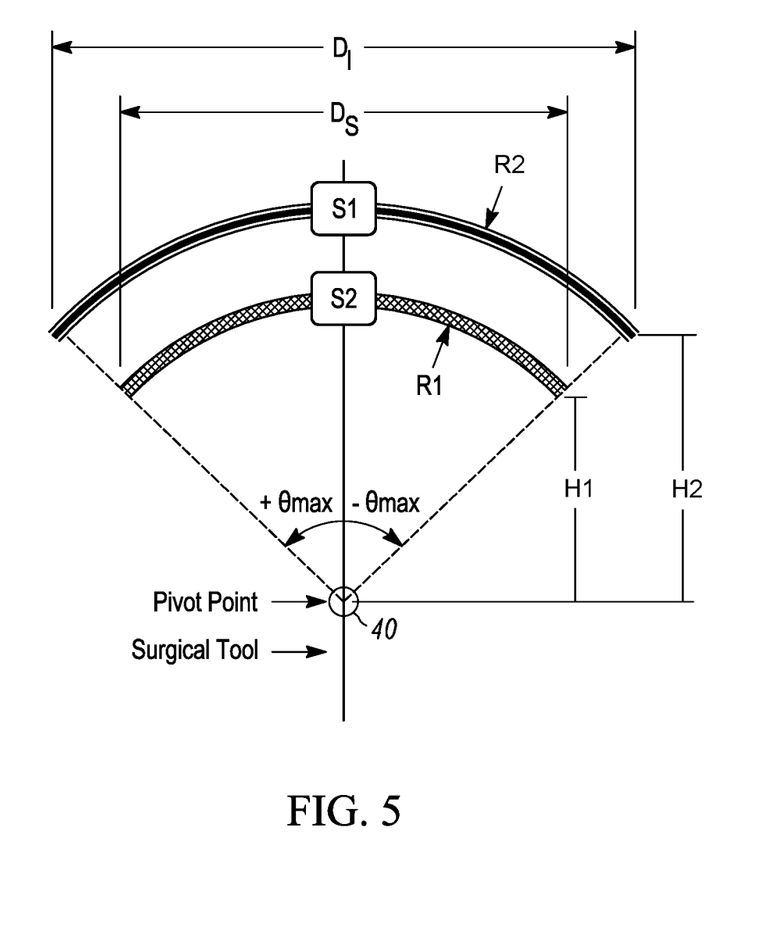
FIG. 5 is a geometrical illustration showing mathematical dimensions of the arcuate links with their respective heights coinciding the centers of curvature of the arcs with the pivot point.

The arcuate links 12 and 14 are adapted such that their center of curvature corresponds with the pivot point 40 of the surgical tool 50. As shown in FIGS. 1 to 4, the second arcuate link 14 is similar in structure to the first arcuate link 12 and is chosen to have a smaller radius (R1) than that of the first link (R2), with the plane of its curvature perpendicular to plane of curvature of the first link. As shown in FIG. 5, this is because the second arcuate link 14 is located below the first arcuate link 12 such that the height distance between the first arcuate link 12 and the desired pivot point (H2) is bigger than the height distance between the second arcuate 14 link and the desired pivot point (H1). Therefore, in order for the respective centers of curvatures of the first and second arcuate links 12 and 14 to coincide at the pivot point 40, the second arcuate link 14 must necessarily have a smaller radius (R1) than the radius (R2) of the first arcuate link 12. The radius of the arcuate links can be modified to adjust their desired distance with respect to the pivot point 40.

When the hub 16 moves (slides) along the second link 14, it will manipulate the tool's orientation in one DoF perpendicular to the first link's 12 DoF. In this architecture, the two arcuate links 12 and 14 will enforce the hub 16, that hosts the surgical tool 50 to move only on the surface of a hemisphere that has it's center kept at the required pivot point 40. The center is defined by the concentric links radii. For each arcuate link 12/14, the separation distance $d_s$ between the parallel curved shafts will define the max dimension of the tool's cross section or thickness.

In order to provide for a 2 DoF manipulator, the manipulator apparatus 10 further comprise a frame 26 having a lateral wall for supporting the extremities of the arcuate links 12 and 14. The manipulator apparatus 10 further comprises guiding means for guiding the extremities of the arcuate links 12 and 14 for enabling simultaneous lateral movement of both the first and second arcuate links 12/14 along the lateral wall of the frame 26. According to one embodiment, the frame comprises a pair of removeably mountable plates 27 defining the lateral wall of the frame.

The frame 26, the guiding means and the arcuate links 12 and 14 are adapted for enabling the hub 16 to be moveable along a movement route within a spherical plane surface having a center of sphere coinciding with the pivot point at any point within the movement route for enabling rotation of the surgical tool about the pivot point in two degrees of freedom defined by the first and second degrees of freedom.

The guiding means can comprise any means for guiding the arcuate links 12 and 14 through the lateral movement supported by the lateral wall of the frame 26 in order to allow the hub to be moveable along a movement route within a spherical plane surface having a center of sphere coinciding with the pivot point at any point within the movement route for enabling rotation of the surgical tool about the pivot point in two degrees of freedom defined by the first and second degrees of freedom.

According to the preferred embodiment, the guiding means comprises two pairs of curved guiding slots 28 and 29, the curved guiding slots 28 and 29 being adapted to engage the extremities of the arcuate links 12 and 14 and to guide them to move (slide) laterally along the route defined by the curved guiding slots 28 and 29. Accordingly, the guiding slots corresponding to each one of the pair of guiding slots 28 and 29 are located opposite to each other symmetrically with respect to the center of the frame. The first pair of guiding slots 28 have a curvature equivalent to the curvature of the second arcuate link 14 and is adapted to guide the first arcuate link 14 through a lateral movement along these slots 28. The second pair of guiding slots 29 have a curvature equivalent to the curvature of the first arcuate link 12 and is adapted to guide the second arcuate link 14 through a lateral movement along these slots 29.

As shown in FIGS. 1 to 4, these slots are preferably curved openings adapted to the form of the extremities of the arcuate links 12 and 14 and located at the lateral wall of the frame 26. A person skilled in the art however should appreciate the guiding slots can have other forms such as curved rails defined by the internal side of the lateral wall of the frame 26.

The guiding means further comprise vertical rollers 34 and 36, and lateral rollers 35 and 37. The guiding means also comprise internal shoulders 30 and external shoulders 32. The rollers (34, 35, 36, 37) are coupled to the extremities of the arcuate links 12 and 14. The rollers 34, 35, 36, 37 can be any suitable type of rollers such as bearings. The vertical rollers 34 and 36 comprise internal vertical rollers 34 located within the frame 26 and external vertical rollers 36 located outside the frame 26. The internal vertical rollers 34 are adapted to engage (roll over) with the internal shoulders 30 in order to enhance the lateral movement of the arcuate links 12 and 14 and prevent downward movement of the arcuate links 12 and 14 particularly while these are in operation (lateral movement). The external vertical rollers 36 are adapted to engage (roll underneath) with the external shoulders 32 to enhance the lateral movement of the arcuate links 12 and 14 and prevent upward movement of the arcuate links 12 and 14 particularly while these are in operation. The cooperation of the vertical rollers 34 and 36 and the shoulders 30 and 32, respectively, prevents any vertical motion of the arcuate links 12 and 14 and therefore assists in keeping the centers of curvature of the arcuate links 12 and 14 stable and fixed during operation.

The lateral rollers 35 and 37 comprise internal lateral rollers 35 located within the frame 26 and adapted to roll over the internal side of the lateral wall of the frame 26 while the arcuate links 12 and 14 are in lateral movement. This enhances the lateral movement of the arcuate links 12 and 14 and prevents external side movement (radially outside the center of the frame) of the arcuate links 12 and 14 particularly while these are in operation (lateral movement). The lateral rollers 35 and 37 further comprise external lateral rollers 37 located outside the frame 26 and adapted to roll over the external side of the lateral wall of the frame 26 while the arcuate links 12 and 14 are in lateral movement. This enhances the lateral movement of the arcuate links 12 and 14 and prevents internal side movement (radially inside the center of the frame) of the arcuate links 12 and 14 particularly while these are in operation (lateral movement).

Depending on the surgical procedure and the used tool 50, the mechanism can be used in three modes: manual, remotely controlled and autonomous modes.

In manual mode, the mechanism is used to provide free rotation of the tool 50 about the entry point in 2 DoF, while preventing any lateral motion of the tool at the point, hence, preventing any enlargement of the port. Example of such tools are the ones used for suturing and knot tying with scissor handles and clippers end effector as shown in FIG. 2.

Also the robot can be used autonomously for precise radioactive seed implantation for prostate and lung brachytherapies, localized drug delivery using needles, catheter insertion, external beam radiation, biopsy sampling, and the like.

The third mode, i.e., remote control mode of the surgical tool can be used for manipulation of laparoscopic cameras and precise tissue removal and other applications.

For the last two modes, the robot can move the tool 50 in precisely controlled motion using 2 micro motors 20 each located at the end of one of the curved links 12/14. Each motor 20 is tied by a cable 21 to the tool adapter block (hub) 16 so it can pull it and drag it to slide along the link 12/14, hence change the orientation of the tool 50. An encoder 22 is placed on the other end of the arcuate link 12/14 to read the motor's angular rotation, which can be utilized to calculate the angular displacement of the tool 50. Actuating the links enables to move the tool autonomously or remotely by means of a joy stick or a graphical user interface (GUI). After it is placed with desired orientation/pose, the tool can be firmly locked in place by 1) connecting the motor to an H-Bridge circuit board and 2) by using a micro motor with a high gearhead ratio (1:1000) to increase the locking/braking force. It is worth mentioning that the link architecture of the robot allows for independent control of the joints so the tool can be manipulated in 1-DoF easily. This is made possible by mounting the motor 20 and the encoder 22 directly on the arcuate link 12/14 hence keeping their locations fixed with respect to the arcuate link 12/14 and its plane. Also, this will obviate the need for any complicated couplings between the driving motor 20 and the driven slide block 16 (hub) other than a simple belt. The robot can be used either in manual, autonomous or remote-control modes to manipulate different kinds of surgical tools necessary for minimally invasive therapy, about a pivot point typically the point of entry of the tool to the patient's internal organs, while preventing lateral enlargement of the pivot point.

Other type of mechanical/electronic mechanisms can be used to automate movement of the arcuate links 12 and 14. For example, mechanical members such as telescopic pistons (not shown) can be provided to apply a force on the hub 16 to force movement along the arcuate links 12/14.

As used herein, the terms "comprises" and "comprising" are to be construed as being inclusive and opened rather than exclusive. Specifically, when used in this specification including the claims, the terms "comprises" and "comprising" and variations thereof mean that the specified features, steps or components are included. The terms are not to be interpreted to exclude the presence of other features, steps or components.

It will be appreciated that the above description related to the invention by way of example only. Many variations on the invention will be obvious to those skilled in the art and such obvious variations are within the scope of the invention as described herein whether or not expressly or explicitly described.

What is claimed:

1. A manipulator apparatus for assisting surgery comprising:

a first arcuate link including a curved portion having a first center of curvature and a first degree of curvature and extending from a first extremity defined at an end of the first arcuate link to a second extremity defined at an opposite end of the first arcuate link, the curved portion of the first arcuate link defining a first arcuate path defined along the curved portion of the first arcuate link;

a hub having a longitudinal axis and adapted to receive and securely hold a surgical tool having a longitudinal axis defined along a length of the surgical tool and a pivot point defined on the longitudinal axis of the surgical tool about which the surgical tool pivots in use, the hub being adapted to be mounted to and engage with the first actuate link to move between the first and second extremities in a first movement route along the first arcuate path such that the first center of curvature coincides with the pivot point of the surgical tool at any point within the first movement route for enabling manipulation of the surgical tool about the pivot point in a first degree of freedom along the first arcuate path;

a second arcuate link including a curved portion having a second center of curvature and a second degree of curvature and extending from a first extremity defined at an end of the second arcuate link to a second extremity defined at an opposite end of the second arcuate link, the curved portion of the second arcuate link defining a second arcuate path defined along the curved portion of the second arcuate link;

the hub being further adapted to be mounted to and engage with the second arcuate link and to move between the first and second extremities of the second arcuate link in a second movement route along the second arcuate path perpendicularly to the first arcuate path such that the second center of curvature coincides with the pivot point of the surgical tool at any point within the second arcuate path for enabling manipulation of the surgical tool about the pivot point in a second degree of freedom along the second arcuate path, the second degree of freedom being perpendicular to the first degree of freedom;

a frame having a lateral wall for supporting the extremities of the arcuate links;

a first motor, a first rotary encoder and a first cable, wherein the hub, the first motor and the first rotary encoder are connected to one another via the first cable, with the first motor and the first rotary encoder being mounted to the first arcuate link in an arrangement wherein the first motor displaces the first cable for actuating non-linear movement of the hub along the second movement route and wherein the first rotary encoder measures the displacement of the first cable for enabling determination of a position of the hub along the first arcuate link;

a second motor, a second rotary encoder and a second cable, wherein the hub, the second motor and the second rotary encoder are connected to one another via the second cable, with the second motor and the second rotary encoder being mounted to the second arcuate link in an arrangement wherein the second motor displaces the second cable for actuating non-linear movement of the hub along the first movement route and wherein the second rotary encoder measures the displacement of the second cable for enabling determination of a position of the hub along the second arcuate link; and guiding means for enabling movement of both the first and second arcuate links along the lateral wall of the frame, wherein the guiding means and the arcuate links are adapted for enabling movement of the hub along a third movement route for enabling displacement of the surgical tool about the pivot point in two degrees of freedom defined by the first and second degrees of freedom, the guiding means including:

a first pair of guiding slots, each guiding slot of the first pair of guiding slots being located on the lateral wall of the frame in an arrangement wherein the guiding slots oppose one another, the first pair of guiding slots having a first degree of curvature equivalent to the degree of curvature of the second arcuate link, the first pair of guiding slots being adapted to slidingly receive the extremities of the first arcuate link for guiding the displacement of the first arcuate link; and a second pair of guiding slots, each guiding slot of the second pair of guiding slots being located on the lateral wall of the frame in an arrangement wherein the guiding slots oppose one another, the second pair of guiding slots having a second degree of curvature equivalent to the degree of curvature of the first arcuate link, the second pair of guiding slots being adapted to slidingly receive the extremities of the second arcuate link for guiding the displacement of the second arcuate link.

2. The manipulator apparatus as claimed in claim 1, wherein the guiding means further comprise vertical rollers and shoulders adapted to engage together for preventing vertical motion of the arcuate links during movement of the hub.

3. The manipulator apparatus as claimed in claim 2, wherein the guiding means further comprise lateral rollers adapted to engage with the lateral wall of the frame for preventing radial motion of the arcuate links during movement of the hub.

4. The manipulator apparatus as claimed in claim 3, wherein each one of the arcuate links comprise a pair of curved rods defining an opening therebetween adapted to allow passage of the surgical tool.

5. The manipulator apparatus as claimed in claim 4, wherein the hub has a lateral wall having openings adapted to receive the arcuate links in a concentric configuration with respect to the longitudinal axis of the hub for allowing the hub to slide along the curved rods in the first and second movement routes.

6. The manipulator apparatus as claimed in claim 5, wherein the hub has substantially a rectangular shape having top and bottom walls and a first and second pairs of opposite side walls forming a lateral wall, wherein the top and bottom walls have openings aligned along the longitudinal axis of the hub for receiving the surgical tool, and each pair of opposite side walls of the hub has aligned openings adapted to receive a particular one of the arcuate links.

7. The manipulator apparatus as claimed in claim 6, further comprising a tool adapter adapted to be adjusted to different types and dimensions of surgical tools, the hub being adapted to receive the surgical tool via the tool adapter.

8. The manipulator apparatus as claimed in claim 1, wherein:

the motors are located at the first extremities of the arcuate links and the rotary encoders are located at the second extremities of the arcuate links.

9. The manipulator apparatus as claimed in claim 1, wherein the first and second centers of curvature are spaced outwardly from an operative lower end of the lateral wall of the frame, thereby to define the pivot point of the surgical tool at a location spaced outwardly from the operative lower end of the lateral wall of the frame.

* * * * *